United States Patent [19]

Granelli et al.

[11] Patent Number: 5,527,961

[45] Date of Patent: Jun. 18, 1996

[54] PROCESS FOR REDUCING THE AMMONIA CONTENT OF A GASEOUS EFFLUENT FROM UREA PRODUCTION PLANTS

[75] Inventors: Franco Granelli; Angelo Corchia, both of Milan, Italy

[73] Assignee: Snamprogetti S.p.A., St. Donato, Italy

[21] Appl. No.: 255,175

[22] Filed: Jun. 7, 1994

[30] Foreign Application Priority Data

Jun. 9, 1993 [IT] Italy .................................. MI93A1216

[51] Int. Cl.⁶ ................................................. C07C 273/16
[52] U.S. Cl. .................................. 564/73; 564/3; 564/67; 504/327
[58] Field of Search .................................. 564/73, 67, 3; 504/327

[56] References Cited

U.S. PATENT DOCUMENTS

| | | | |
|---|---|---|---|
| 3,333,939 | 8/1967 | Davis et al. | 71/29 |
| 3,535,376 | 10/1970 | Scheirer et al. | 564/3 |
| 3,689,551 | 9/1972 | Patterson et al. | 564/3 |
| 3,928,015 | 12/1975 | Siegel et al. | 71/28 |
| 4,461,913 | 7/1984 | Lewis et al. | 564/73 |

FOREIGN PATENT DOCUMENTS

| | | | |
|---|---|---|---|
| 1912125 | 10/1969 | Germany | 564/73 |
| 844294 | 11/1958 | United Kingdom . | |

OTHER PUBLICATIONS

Patent Abstracts of Japan, vol. 11, No. 38, Feb. 4, 1987; Japanese Patent Abstract 6120419.

*Primary Examiner*—Shailendra Kumar
*Attorney, Agent, or Firm*—George P. Hoare, Jr.; Rogers & Wells

[57] ABSTRACT

A process for neutralizing the ammonia present in the molten urea originating from the concentration section of a plant for its production, comprising adding to the molten urea a small quantity of an acid.

7 Claims, 1 Drawing Sheet

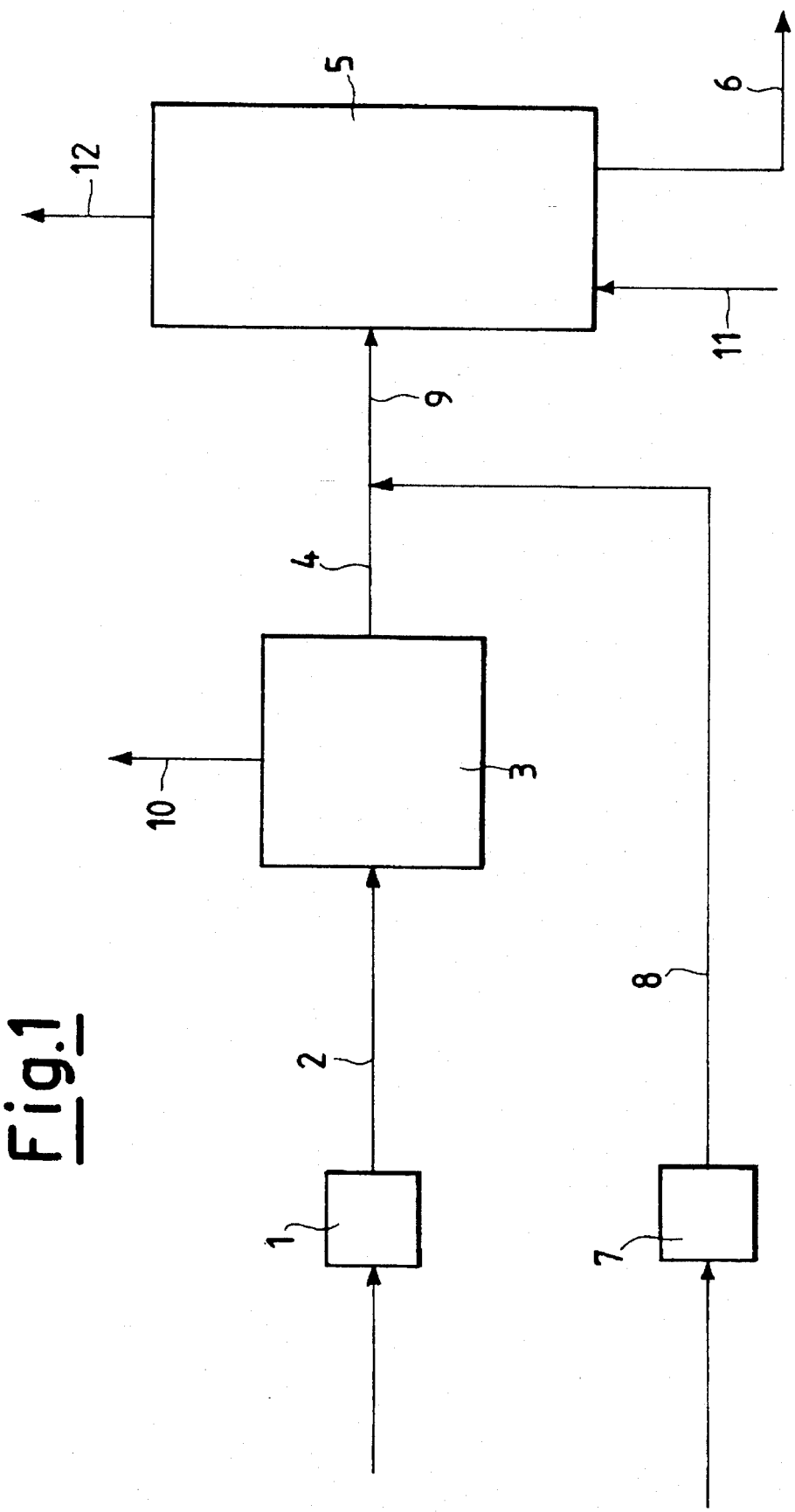

PROCESS FOR REDUCING THE AMMONIA CONTENT OF A GASEOUS EFFLUENT FROM UREA PRODUCTION PLANTS

BACKGROUND OF THE INVENTION

This invention relates to a process for reducing the ammonia content of a gaseous effluent from urea production plants. All industrial urea production plants are based on the following direct synthesis reaction starting from ammonia and carbon dioxide:

$$2NH_3+CO_2=CO(NH_2)_2+H_2O$$

In industrial plants of total recycle type the ammonia, generally liquid, and the carbon dioxide, generally gaseous, are fed in quantities slightly exceeding the stoichiometric values. The difference is due to ammonia and carbon dioxide losses which, either as such or in the form of urea, escape to atmosphere and can pollute the environment.

Said losses can be continuous or discontinuous, liquid or gaseous, the latter possibly containing solid products (urea) or gaseous products (ammonia).

All can result in environmental pollution of a more or less serious extent depending on the amount of loss and the plant position (extent of area population), and is continuously monitored to satisfy local regulations, which vary greatly but in general tend to become increasingly restrictive.

It is therefore important to provide a process which virtually nullifies the ammonia content of a gaseous effluent from industrial urea production plants, so nullifying its pollutant effect.

In said plants, after a reaction stage and a number of recycle stages the aforesaid reaction leads to an aqueous urea solution of about 75 wt % concentration which still contains a small percentage of ammonia which has not been converted into urea.

This solution is concentrated to 96–99.8 wt %, during which concentration a large part of the ammonia is removed from the solution together with the water, and is recovered in the plant. The final solution, practically in the form of molten urea, still contains a small percentage of ammonia, which during the final concentration stage is increased by a further quantity which forms during said final concentration stage by the effect of the reaction:

$$2CO(NH_2)_2=NH_2\text{-}CO\text{-}NH\text{-}CO\text{-}NH_2+NH_3$$

which results in one mole of biuret plus one mole of ammonia from two moles of urea.

After said final concentration stage, the urea solution (molten urea) still containing ammonia but in a quantity of the order of 0.1 wt % or less is solidified into small beads, the solid product obtained being known as prilled urea if solidification is by a prilling process, or granulated urea if solidification is by a granulating process.

Both said solidification processes consist of bringing the molten urea, divided into droplets in the case of prilling or finely sprayed onto a mass of beads which enlarge in the case of granulation, into contact with an air stream which removes the heat of solidification, dries the product in the case of granulation using 96 wt % molten urea as feed, and finally cools the solid beads to a temperature substantially less than solidification temperature. At the end of the solidification stage the solid product obtained, either prilled or granulated urea, contains a certain quantity of free ammonia (60–200 ppm), the remaining ammonia which was contained in the molten urea having been transferred to the solidification and cooling air and hence fed to atmosphere with pollutant effect.

The ammonia content of this air is very small (80–200 ppm), which explains why it was not a problem up to a short time ago. As pollution problems have generally become more sensitive with consequent more restrictive regulations, it has become necessary to eliminate or at least drastically reduce ammonia emission into the atmosphere.

This problem is not easy to solve because the ammonia quantity contained in the air is relatively small. Washing with water is virtually ineffective because of the low partial pressure of the ammonia in the air.

In existing plants for the wet removal of urea particles contained in this air it has been found that they are totally ineffective against ammonia. In addition the air volume concerned is very large, with the result that the equipment required for its removal would be bulky. In this respect, for a 1000 t/d prilled urea plant, this being an average size, 400,000–500,000 $Nm^3$/h of air are required.

The situation is aggravated by the fact that the air is fed to atmosphere at a distance from the ground which can reach 60–80 meters, so that in providing a removal plant it would be necessary to convey this large air quantity to ground level, with further investment and operating cost, this latter because of the considerable pressure drop.

In the case of granulation plants, in which the air throughput to be treated is substantially less than in the case of prilling, plants for removing ammonia from the air already exist. They comprise washing with water made slightly acid by the addition of sulphuric acid.

Their removal efficiency is reasonable, but the resultant water quantity is considerable and contains a small percentage of the corresponding salt, which has to find an easy accommodation and in any event involves operating costs for its concentration.

SUMMARY OF THE INVENTION

The applicant has now found a process which solves the problem of the ammonia present in the air originating from a prilling tower or a granulation section, with minimal investment and operating costs.

Consequently the present invention provides a process for neutralizing the ammonia present in the molten urea originating from the concentration section of a plant for its production, comprising adding to the molten urea a small quantity of an acid. Preferably the acid is inorganic, is chosen from sulphuric acid and phosphoric acid and is used in a quantity of between 0.25 and 0.45 wt % on the molten urea.

The acid neutralizes both the ammonia present and that which forms as a result of the said formation of biuret.

The quantity of ammonium sulphate or phosphate which forms remains in the solid prilled or granulated product in an extremely small percentage (3000–6000 ppm) and such as not to have any negative influence on the physical characteristics of the solid product, which can be used normally either as a fertilizer or as a product for industry, although in this case at least for certain products the necessary check should be made.

The acid could also be added further upstream, for example before the final vacuum concentration section.

However in this case a much larger acid quantity would be required for neutralizing all the ammonia contained in the urea solution. The final result would be an ammonium salt content in the solid urea product of the order of 8–9%.

The urea produced would not then be suitable for industrial uses but could have advantages for agricultural use in soil deficient in sulphur.

DESCRIPTION OF THE PREFERRED EMBODIMENTS AND THE DRAWINGS

FIG. 1 shows the schematic flow diagram of the process of the present invention in the case of a prilling plant. The 67–75 wt % urea solution, containing small percentages of ammonia and carbon dioxide, is fed by the pump 1 through the line 2 to the concentration section 3 (generally in one or more vacuum stages), The urea solution concentrated to 99.4–99.8 wt %, hence virtually molten urea, is fed to the top of the prilling tower 5 where it is sprayed to form urea droplets, which then solidify in the form of beads (prilled urea).

However before the molten urea reaches the top of the prilling tower an adecruate metered quantity of sulphuric acid concentrated to 98–99 wt % is added to it by the metering pump 7 via the line 8.

If phosphoric acid is used it may be preferable to shift the injection point more upstream, ie before the last vacuum concentration stage, because phosphoric acid when concentrated (54 wt % of $P_2O_5$ or about 75 wt % of $H_3PO_4$) contains a larger quantity of water.

During its flow through the line 9 the added acid neutralizes both the ammonia present in the molten urea and that which forms together with the biuret, as already stated.

A suitable mixer (not shown in FIG. 1) can also be installed where the line 8 meets the line 4.

Vapour essentially in the form of steam containing a small percentage of ammonia, carbon dioxide and urea particles leaves the concentration section 3 via the line 10.

Both the ammonia and the urea can be completely recovered and recycled to the synthesis section of the urea plant.

To transform the molten urea into solid beads, the air required for extracting the heat of solidification and for cooling enters the base of the prilling tower 5 via the line 11 and leaves from the top of the prilling tower via the line 12 where it is fed to atmosphere (the prilling tower can be of natural or forced draught type).

The presence of gaseous ammonia in this air is hence limited to a few mg per $Nm^3$ (maximum 8) and is therefore less than the most restrictive regulation relative to atmospheric pollution.

Two non-limiting examples are given hereinafter to better illustrate the invention.

EXAMPLE 1

In a plant for producing 15000 kg/h of prilled urea from ammonia and carbon dioxide, the urea solution produced by the synthesis section has the following composition:

|  | kg/h | wt % |
| --- | --- | --- |
| Urea | 14820 | 69.40 |
| Biuret | 85 | 0.40 |
| $NH_3$ | 344 | 1.61 |
| $CO_2$ | 158 | 0.74 |
| $H_2O$ | 5947 | 27.85 |
| Total | 21354 | 100.00 |

In a concentration section, from which vapour is released consisting of:

|  | kg/h | wt % |
| --- | --- | --- |
| Urea | traces |  |
| $NH_3$ | 333 | 5.20 |
| $CO_2$ | 158 | 2.50 |
| $H_2O$ | 5910 | 92.30 |
| Total | 6401 | 100.00 | and from which the ammonia and carbon dioxide are completely recovered and recycled to the synthesis section, molten urea is obtained composed of:

|  | kg/h | wt % |
| --- | --- | --- |
| Urea | 14771 | 98.78 |
| Biuret | 127 | 0.85 |
| $NH_3$ | 18 | 0.12 |
| $H_2O$ | 37 | 0.25 |
| Total | 14953 | 100.00 |

53 kg/h of a 98.0 wt % sulphuric acid solution are added to this molten urea by a metering pump feeding into the line leading to the top of the prilling tower, which is of natural draught type. From the base of the prilling tower a product is extracted formed from:

|  | kg/h | wt % |
| --- | --- | --- |
| Urea | 14759 | 98.39 |
| Biuret | 133 | 0.89 |
| $H_2O$ | 38 | 0.25 |
| $(NH_4)_2SO_4$ | 70 | 0.47 |
| Total | 15000 | 100.00 |

As can be seen, the water quantity introduced into the molten urea by the acid solution only negligibly increases the water content of the final product.

The air discharged from the top of the prilling tower, 56 meters high, is about 150,000 $Nm^3/h$, its ammonia content is about 5 $mg/Nm^3$ and its urea content about 40 $mg/Nm^3$.

Without the addition of the acid solution, said ammonia content under identical operating conditions had been found to be 180 $mg/Nm^3$.

EXAMPLE 2

In a plant for producing 62500 kg/h of prilled urea from ammonia and carbon dioxide, the urea solution produced by the synthesis section has the following composition:

|  | kg/h | wt % |
| --- | --- | --- |
| Urea | 61830 | 68.98 |
| Biuret | 315 | 0.35 |
| $NH_3$ | 1552 | 1.73 |
| $CO_2$ | 692 | 0.77 |
| $H_2O$ | 25251 | 28.17 |
| Total | 89640 | 100.00 |

In a concentration section, from which vapour is released consisting of:

|       | kg/h   | wt %  |
| --- | --- | --- |
| Urea  | traces |       |
| $NH_3$ | 1515   | 3.55  |
| $CO_2$ | 692    | 2.54  |
| $H_2O$ | 25095  | 91.91 |
| Total | 27302  | 100.00 | and from which the ammonia and carbon dioxide are completely recovered and recycled to the synthesis section, molten urea is obtained composed of:

|       | kg/h  | wt %  |
| --- | --- | --- |
| Urea  | 61652 | 98.90 |
| Biuret | 468  | 0.75  |
| $NH_3$ | 62   | 0.10  |
| $H_2O$ | 156  | 0.25  |
| Total | 62338 | 100.00 |

189 kg/h of a 98.0 wt % sulphuric acid solution are added to this molten urea by a metering pump feeding into the line leading to the top of the prilling tower, which is of natural draught type. From the base of the prilling tower a product is extracted formed from:

|       | kg/h  | wt %  |
| --- | --- | --- |
| Urea  | 61598 | 98.55 |
| Biuret | 493  | 0.79  |
| $H_2O$ | 159  | 0.26  |
| $(NH_4)_2SO_4$ | 250 | 0.40 |
| Total | 62500 | 100.00 |

As can be seen, the water quantity introduced into the molten urea by the acid solution only negligibly increases the water content of the final product.

The air discharged from the top of the prilling tower, 58 meters high, is about 620,000 $Nm^3/h$, its ammonia content is 4 $mg/Nm^3$ and its urea content is 40 $mg/Nm^3$.

Without the addition of the acid solution, said ammonia content under identical operating conditions had been found to be 160 $mg/Nm^3$.

We claim:

1. A process for neutralizing the ammonia present in the molten urea originating from the concentration section of a plant for its production, comprising adding to the molten urea a small quantity of an inorganic acid wherein said quantity is between about 0.25% and 0.45% based on the weight of the molten urea.

2. A process as claimed in claim 1, wherein the acid is chosen from the group consisting of sulfuric acid and phosphoric acid.

3. A process for limiting the ammonia content of a gaseous effluent from a urea solidification section of a urea production plant to a maximum of about 8 $mg/Nm^3$, which comprises concentrating an aqueous urea solution in a vacuum concentration section to obtain molten urea containing at least 96% by weight of urea and residual ammonia, transferring said molten urea to said solidification section, and solidifying the molten urea by contact with an air stream to obtain substantially pure solid urea, wherein an acid selected from the group consisting of sulfuric acid and phosphoric acid is added to said molten urea before it enters said solidification section, in an amount comprised from about 0.25% to 0.45% by weight based on the weight of the molten urea.

4. A process according to claim 3, wherein the residual ammonia contained in said molten urea is 0.1% by weight or less.

5. A process according to claim 3, wherein the solidification section is a prilling section or a granulating section.

6. A process according to claim 3, wherein said substantially pure solid urea contains from about 0.3% to 0.6% by weight of ammonium phosphate or sulphate.

7. A process according to claim 1, wherein after said molten urea is treated with said inorganic acid, it is solidified by contact with an air stream to obtain substantially pure solid urea, whereby the ammonia content of an ensuing gaseous effluent containing said solid urea is limited to a maximum of about 8 $mg/Nm^3$.

* * * * *